United States Patent [19]
Fritz et al.

[11] Patent Number: 5,407,915
[45] Date of Patent: Apr. 18, 1995

[54] HUMAN BIKUNIN VARIANTS AS PROTEINASE INHIBITORS, AND MEDICAMENTS CONTAINING THESE

[75] Inventors: Hans Fritz, Hohenbrunn; Wolfgang Gebhard, Unterumbach; Rathindra Das, Wuppertal, all of Germany

[73] Assignee: Bayer Aktiengesellschaft, Leverkusen, Germany

[21] Appl. No.: 27,602

[22] Filed: Mar. 5, 1993

Related U.S. Application Data

[63] Continuation of Ser. No. 517,792, May 1, 1990, abandoned.

[30] Foreign Application Priority Data

May 13, 1989 [DE] Germany ............ 39 15 689.3
Jan. 18, 1990 [DE] Germany ............ 40 01 244.1

[51] Int. Cl.⁶ .................. A61K 37/02; C12P 21/02; C07K 13/00
[52] U.S. Cl. .................. 514/12; 435/69.2; 530/350
[58] Field of Search ............ 530/350; 514/12; 435/69.2

[56] References Cited

U.S. PATENT DOCUMENTS 4,595,674  6/1986  Tschesche et al. .......... 514/9

FOREIGN PATENT DOCUMENTS 0255011  2/1988  European Pat. Off.

OTHER PUBLICATIONS

Darnell et al., Molecular Cell Biology, Freeman and Company, 1986, 258–260 and 55.
Hochstrasser et al "Kunitz-Type Proteinase Inhibitors . . . " Biol. Chem. Hoppe Seyler, v. 366 pp. 473–478, May, 1985.
Travis & Salvesen, Ann. Rev. Biochem 52, 655, 1983.
Matheson et al., J. Biol. Chem. 261, 10404, 1986.
Courtney et al., Nature 313, 149, 1985.
Schreitmuller et al, Biol. Chem. Hoppe-Seyler, 368, 963, 1987.
Gebhard et al., Biol. Chem. Hoppe-Seyler 369, 19, 1988.
Gebhard et al., FEBS Lett. 229, 63, 1988.
Gebhard et al., Euro. J. Biochem. 181, 571 1989.
Kaumeyer et al., Nucleic Acids Res. 14, 7839 (1986).
Gebhard & Hochstraber in: Proteinase Inhibitors, Barrett & Salvesen, eds., Elsevier, 1986, p. 375.
Vetr et al., FEBS Lett. 245, 137, 1989.
M. W. Swaim et al, "Modification of the tandem reactive centres of human . . . ", Biochem. J., V. 254, pp. 171–178, 1988.
K. Hochstrasser et al, "Kunitz-Type Proteinase Inhibitors Derived by . . . ", Biol. Chem. Hoppe Seyler, V. 366, pp. 473–478, May 1985.
M. Courtney et al, "Synthesis in E. coli of alpha 1-antitrypsin . . . ", Nature, V. 313, pp. 149–151, Jan. 1985.

Primary Examiner—Garnette D. Draper
Assistant Examiner—Sally P. Teng
Attorney, Agent, or Firm—Sprung Horn Kramer & Woods

[57] ABSTRACT

A proteinase inhibitor which has the sequence of amino acids 21 to 147 of human bikunin, in which at least one amino acid residue has been replaced by another naturally occurring amino acid. Such proteinase inhibitor is useful in pharmaceutical compositions.

16 Claims, 13 Drawing Sheets

```
                                                    20
                              10                 
        AVLPQEEEGSGGGQLVTEVTK
22                  30      ‡ ‡ 40          50                    60                    70       77
KEDSCQLGYSAGPCMGMTSRYFYNGTSMACETFQYGGCMGNGNNFVTEKECLQTCR
    ⌒                    ———              —              —    ——
                            90  ‡    ‡         100                110              120                   133
78 80                                                                                              ——  ——
TVAACNLPIVRGPCRAFIQLWAFDAVKGKCVLFPYGGCQGKGNKFYSEKECREYCG
  ⌒
            140       147
VPGDGDEELLRFSN
```

FIG. 1

```
NcoI        22                        30                   36
     M  V  T  K  K  E  D  S  C  Q  L  G  Y  S  A  G  P  C  M
    <---------------------1-------------------------X---
    CCATGGTAACTAAAAAAGAAGACTCTTGCCAGCTGGGCTACTCTGCTGGTCCGTGCATGG    60
        CATTGATTTTTTCTTCTGAGAACGGTCGACCCGATGAGACGACCAGGCACGTACC
        <------------4-----------X---------------5------------

Module 1 <  >  Module 2
    38    40                Asp718    50
    G  M  T  S  R  Y  F  Y  N  G  T  S  M  A  C  E  T  F  Q  Y
    -2-----X---------3--------X--------------------7-------------
    GTATGACTTCTCGTTACTTCTACAACGGTACCTCTATGGCTTGCGAAACTTTCCAGTACG   120
    CATACTGAAGAGCAATGAAGATGTTGCCATGGAGATACCGAACGCTTTGAAAGGTCATGC
    -X-------------6-------------X----------------------10-----

60                   70
    G  G  C  M  G  N  G  N  N  F  V  T  E  K  E  C  L  Q  T  C
    -X------------------8------------------X----------------9----
    GTGGTTGCATGGGTAACGGTAACAACTTCGTTACTGAAAAAGAATGCCTGCAGACTTGCC   180
    CACCAACGTACCCATTGCCATTGTTGAAGCAATGACTTTTTCTTACGGACGTCTGAACGG
    ---------------- X-----------11---------------X--------12----

R endendend SalI
    ----------->
    GTTAATGATAG
    CAATTACTATCAGCTG                                                196
    --------------->
```

FIG. 2

```
 78   80                                     90   92   94       97
  T  V  A  A  C  N  L  P  I  V  R  G  P  C  R  A  F  I  Q  L
                                            <------A---------------
ACTGTGGCGGCCTGCAATCTCCCCATAGTCCGGGGCCCCTGCCGAGCCTTCATCCAGCTC
TGACACCGCCGGACGTTAGAGGGGTATCAGGCCCCGGGGACGGACCGGAAGTAGGTCGAG
                                            <----------B---------------

100                              110
  W  A  F  D  A  V  K  G  K  C  V  L  F  P  Y  G  G  C  Q  G
------------------------X----------C------------------------
TGGGCATTTGATGCTGTCAAGGGGAAGTGCGTCCTCTTCCCCTACGGGGGCTGCCAGGGC
ACCCGTAAACTACGACAGTTCCCCTTCACGCAGGAGAAGGGGATGCCCCCGACGGTCCCG
--------------X----------------------D------------------------

120                           130
  N  G  N  K  F  Y  S  E  K  E  C  R  E  Y  C  G  V  P  G  D
------------>
AACGGGAACAAGTTCTACTCAGAGAAGGAGTGCAGAGAGTACTGCGGTGTCCCTGGTGAT
TTGCCCTTGTTCAAGATGAGTCTCTTCCTCACGTCTCTCATGACGCCACAGGGACCACTA
------------>

140              147
  G  D  E  E  L  L  R  F  S  N
GGTGATGAGGAGCTGCTGCGCTTCTCCAACTGACAACTGGCCGGTCTGCAAGTCAGAGGA
CCACTACTCCTCGACGACGCGAAGAGGTTGACTGTTGACCGGCCAGACGTTCAGTCTCCT

TGGCCAGTGTCTGTCCCGGGGTCCTGTGGCAGGCAGCGCCAAGCAACCTGGGTCCAAATA
ACCGGTCACAGACAGGGCCCCAGGACACCGTCCGTCGCGGTTCGTTGGACCCAGGTTTAT

AAAACTAAATTGTAAACTCCTGAAAAAAAAAAAAAAAAA
TTTTGATTTAACATTTGAGGACTTTTTTTTTTTTTTTTT
```

FIG. 6

HUMAN BIKUNIN VARIANTS AS PROTEINASE INHIBITORS, AND MEDICAMENTS CONTAINING THESE

This application is a continuation of application Ser. No. 517,792, filed May 1, 1990, now abandoned.

BACKGROUND OF THE INVENTION

1. Field of the Invention

The invention embraces peptide variants based on the domains having inhibitory activity of human bikunin (that is to say the component having inhibitory activity of inter-α-trypsin inhibitor, or the acid-stable serum trypsin inhibitor, or the urinary trypsin inhibitor), process for preparing the described peptide variants by methods of genetic manipulation using microorganisms (bacteria, lower eukaryotes), as well as medicaments containing these peptide variants. The peptide variants are characterized by their ability to inhibit serine proteases, for example, pancreatic and granulocytic elastase, cathepsin G or plasma kallikrein.

2. Description of Related Art

When proteases reach the extracellular space they are normally rapidly trapped by potent endogenous proteinase inhibitors such as $\alpha_1$-proteinase inhibitor (Travis & Salvesen, Ann. Rev. Biochem., 52, 655, 1983). In certain situations this protective mechanism may not operate or at least not operate adequately, and the consequence may be serious pathological states such as the development of emphysema, septic shock, shock lung, ARDS, rheumatoid arthritis, coagulation disorders, kidney and liver failure, inter alia. Proteinase inhibitors with a specific action are of special interest in this connection as potential therapeutics. The proteinase inhibitors which are of particular interest for use in humans have amino acid sequences similar to natural human inhibitors. This particularly applies to long-term therapies such as the treatment of $\alpha_1$-proteinase inhibitor deficiencies (development of emphysema) to prevent toxic or allergic side effects.

Although $\alpha_1$-proteinase inhibitor is the natural antagonist of neutrophilic elastase, whose extracellular inhibition is the primary aim in an inflammatory event, it is not optimally suited for therapeutic use for several reasons. Its relatively high molecular weight of 53,000 d would require the use of unphysiologically large amounts by weight of the inhibitor. Although the required amounts could be obtained by genetic engineering means, it would be necessary to use even larger amounts of the inhibitor because of the reduced biological half-life in the circulation of a recombinant protein which is not glycosylated in the physiological manner (Matheson et al., J. Biol. Chem., 261, 10404, 1986). In any event, the inhibitor is regarded as susceptible to proteolysis and oxidation.

Both properties further reduce the concentration of the active species. Only the susceptibility to oxidation could be eliminated by genetic engineering means by replacing the methionine residue in the reactive center of the inhibitor ($P_1$ position) by, for example, leucine (McCourtney et al., Nature, 313, 149, 1985).

The aim of the present invention is to develop proteinase inhibitors, for example, against human leukocyte elastase, cathepsin G or plasma kallikrein having a distinctly lower molecular mass for the treatment of human diseases. In this connection, the aim was to examine whether it is possible to tailor proteinase inhibitors to have a desired inhibitory spectrum by modification of currently known human inhibitors. Conceivable as suitable basic molecules for this would be the subunit having inhibitory activity of human inter-α-trypsin inhibitor ITI (Schreitmüller et al., Biol. Chem. Hoppe-Seyler, 368, 963, 1987; Gebhard et al., Biol. Chem. Hoppe-Seyler, 369S, 19, 1988; Gebhard et al., FEBS Lett., 229, 63, 1988; Gebhard et al.; Euro. J. Biochem., in press), which is called bikunin hereinafter (FIG. 1), as well as the Kunitz-type trypsin inhibitors of identical structure in the serum (STI) and the urine (UTI), if it were possible by replacing a few amino acid residues to achieve a specific alteration of the natural inhibitory spectrum of these inhibitors (FIG. 1). They are the result of the proteolytic maturation of the primary translation product of a single gene (Kaumeyer et al., Nucleic Acids Res. 14, 7839, 1986) and consist of a N-terminal peptide which can be eliminated with trypsin (amino acid residues 1–21) and two consecutive, structurally related domains (domain 1 is the N-terminal domain, defined as amino acid residues 22–77, and domain 2 is the C-terminal part of the protein, defined as amino acid residues 78–147), and these can also be obtained singly by treatment with trypsin. Both domains have proteinase-inhibitory activity of differing inhibitory specificity (Gebhard & Hochstraβer in: Proteinase Inhibitors, Barrett & Salvesen, eds., Elsevier, 1986, p 375).

Depending on the particular physiological situation, the acute-phase protein bikunin may be present both in complexed form (in ITI or in a complex with immunoglobulins) and in non-complexed form, which is then detectable as STI. UTI is STI which has undergone renal filtration. Accordingly, the individual inhibitors differ only in that they are either associated with other proteins or not, or are detected in different body fluids.

The specific and potent inhibitors of, for example, neutrophilic elastase, cathepsin G or plasma kallikrein based on bikunin domains could be obtained by replacing the amino acid residues in position PI of the reactive centers of domain 1 or domain II of the inhibitor. Furthermore, additional replacements in the domains, for example, in the particular $P_2'$ position, are able to improve the inhibitory properties additionally.

SUMMARY OF THE INVENTION

Accordingly, the present invention relates generally to variants of Kunitz-type inhibitors whose inhibitory spectra have been altered because of the replacement of a natural amino acid residue, not only in position $P_1$, but also in the $P_2^1$ position of the reactive center, by another natural amino acid residue, specifically to those inhibitors which have been obtained on the basis of the single domains, or the domains linked to one another, of human bikunin, as long as the inhibitory properties of the natural inhibitor or of its individual domains have been altered and/or improved by replacement of the natural amino acid residues in positions $P_1$ and/or $P_2'$ of the reactive centers of one or both domains by any of the natural amino acids, but in particular by amino acids from the group comprising Ala, Gly, Ile, Leu, Arg, Phe, Val, Tyr, Trp and Lys. Furthermore, the invention also relates to the gene constructions forming the basis for the inhibitor variants, irrespective of the particular choice of codons and the linkage of regions of natural cDNA with such synthetic DNA.

Furthermore, the present invention also relates to bikunin variants in which, besides replacements in one or both $P_1$ positions, as well as in one or both $P_2'$ positions, there are also other replacements in other positions. Additional replacements of this type may further improve the desired inhibitory properties, result in more favorable pharmacokinetic behavior, prolong the in vivo half-life or result in the industrial preparation being more favorable.

Finally, the present invention also embraces bikunin variants having N-terminal and C-terminal peptide segments which differ, in nature and extent, apart from the cysteine residues in positions 26 and 76 (inhibitor domain 1) and 82 and 132 (inhibitor domain 2) which are necessary for the formation of the basic structures. The originally defined domain limits ($Lys^{22}$ and $Arg^{77}$ of inhibitor domain 1 and $Thr^{78}$ and $Asn^{147}$ of inhibitor domain 2) had been defined on the basis of the division into functional peptides which can be achieved with trypsin, and do not coincide exactly with the exon regions which have now been determined (Vetr et al., FEBS Lett. in the press, 1989). According to this, the two inhibitor domains would be limited by the amino acid residues $Asp^{24}$ and $Val^{79}$, and $Ala^{80}$ and $Asp^{137}$, respectively (FIG. 1). Depending on the expression system used, individual gene constructions may code for N- or C-terminal peptide extensions, irrespective of whether these are retained, in whole or in part, in the final inhibitor variant and merely function temporarily as part of a precursor protein and whether these extensions can be assigned to natural bikunin or to a foreign protein.

For example, the N-terminal sequence $Met^{18}$-$Thr^{19}$-$Val^{20}$-$Lys^{21}$, which is identical to the natural amino acid sequence of bikunin apart from the methionine residue, can advantageously be used to obtain, by cleavage with trypsin, a single product which corresponds to the composition of the original defined domain 1. It is also possible in this way smoothly to remove bikunin domains from constructions with an N-terminal foreign protein segment. On direct expression (without an N-terminal foreign protein segment) there may also be expected to be partial, or even complete under certain conditions, elimination of the N-terminal methionine. To prevent the possibility of removal of the C-terminal arginine on single-headed constructions of domain 1 in therapeutic applications, in some circumstances C-terminal extensions are preferred.

The present invention concerns a proteinase inhibitor which has amino acids 21 to 147 of human bikunin, in which at least one amino acid residue has been replaced by another naturally occurring amino acid. The replacement is preferably at one or more of positions 36, 38, 45, 92, 94, 98 or 116.

Preferred replacements are as follows:
Position 36: Met by Leu, Ile, Val, Arg, Phe, Tyr, Trp or Lys,
Position 38: Met by Leu, Arg, Ile, Val or Lys,
Position 45: Asn by another natural amino acid,
Position 92: Arg by Leu, Ile, Val, Phe or Lys,
Position 94: Phe by Leu, Arg, Lys, Ile or Val,
Position 98: Trp by Tyr, Lys, Ile, Val, Phe, Leu, Ala, Gly or Ser
Position 116: GIN by Arg or Lys.

Furthermore, one or more Met residues can be replaced by a nonoxidizable amino acid residue.

The proteinase inhibitor of the invention can also have an additional polypeptide at the N-terminus whose amino acid sequence is derived from the natural sequence 1 to 21 of bikunin.

DETAILED DESCRIPTION OF THE INVENTION

The expression of variants of bikunin or of fragments of bikunin variants can be carried out successfully with bacterial or eukaryotic systems. Thus, suitable among bacterial systems is, for example, expression in *Escherichia coli* K 12 strains; either in unfused form in the cytoplasm, as fusion protein formed within the cell and connected to a suitable fusion partner, for example the N-terminal part of MS2 replicase, or else as a product which has inhibitory activity and is secreted into the periplasmic space by using suitable signal peptides, for example of the OmpA signal sequence.

Suitable among the eukaryotic systems are, for example, yeast secretion systems in which the expression product is conveyed by a suitable leader sequence, for example the alpha factor pre-pro-sequence, through the secretion route and is released into the culture medium as substance having inhibitory activity. It is furthermore possible to use yeast expression systems which result in intracellular synthesis.

However, it is additionally possible to use many other pro- and eukaryotic expression systems, for example using strains of Bacillus, Staphylococcus, Hansenula, Aspergillus or other host strains.

If the aim is to achieve glycosylation similar to that present in mammals, systems which glycosylate correctly must be chosen. Non-glycosylated bikunin variants are obtained in prokaryotic expression systems. Yeast expression systems usually result in a glycosylation which differs from the mammalian glycosylation pattern. Non-glycosylated bikunin variants obtained with yeast expression systems can be prepared by use of deglycosylating enzymes or by expression of variants which cannot be glycosylated.

The present invention includes pharmaceutical preparations which in addition to non-toxic, inert pharmaceutically suitable excipients contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, coated tablets, capsules, pills, suppositories and ampoules, of which the content of active substance corresponds to a fraction or a multiple of an individual dose. The dosage units can contain, for example, one, two, three or four individual doses or one half, one third, or one quarter of an individual dose. An individual dose preferably contains the amount of active compound which is given in one administration and which usually corresponds to a whole, a half or a third or a quarter of the daily dose.

By non-toxic inert pharmaceutically suitable excipients there are to be understood solid, semi-solid or liquid diluents, fillers and formulation auxiliaries of all kinds.

Tablets, coated tablets, capsules pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary excipients such as (a) fillers and extenders, for example starches, lactose, sucrose, glucose, mannitol and silica, (b) binders, for example, carboxymethylcellulose, alginates, gelatine and polyvinylpyrrolidone, (c) humectants, for example, glycerine, (d) disintegrating agents, for example, agar-agar, calcium carbonate and sodium carbonate, (e) solution retarders, for example, paraffin, and (f) absorption accelerators, for example, quaternary ammonium compounds, (g) wetting agents, for example, cetyl alcohol or glycerine monostearate, (h) absorbents, for example, kaolin and bentonite, and (i) lubricants, for example, talc, calcium stearate and magnesium stearate and solid polyethylene glycols, or mixture of the substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example, polyethylene glycols, fats, for example, cacao fat, and higher esters (for example $C_{14}$-alcohol with $C_{16}$-fatty acid) or mixtures of these substances.

Ointments, pastes, creams and gels can contain the customary excipients in addition to the active compound or compounds, for example, animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example, lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such a solvents, solubilizing agents and emulsifiers, for example, water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerine, glycerineformal, tetrahydrofurfuryl alcohol, polyethylene glycols and fatty acid esters of sorbitan, or mixtures of these substances.

For parenteral administration, the solutions and emulsions can also be in sterile form which is isotonic with blood.

Suspensions can contain the customary excipients in addition to the active compound or compounds, such as liquid diluents, for example, water, ethyl alcohol or propylene glycol, suspending agents, for example ethoxylated isostearyl alcohols, polyoxyethylene sorbitol esters and sorbitan esters, microcrystalline cellulose, aluminium meta-hydroxide, bentonite, agar-agar and tragacanth or mixtures of these substances.

The formulation forms mentioned can also contain dyestuffs, preservatives and additives which improve the odor and flavor, for example, peppermint oil and eucalyptus oil, and sweeteners, for example, saccharin.

The therapeutically active compounds should preferably be present in the abovementioned pharmaceutical preparations in a concentration of 0.1 to 99.5% by weight, preferably of about 0.5 to 95% by weight of the total mixture.

The abovementioned pharmaceutical preparations can also contain other pharmaceutical active compounds in addition to the compounds according to the invention.

The abovementioned pharmaceutical preparations are manufactured in the usual manner according to known methods, for example, by mixing the active compound or the active compounds with the excipient or excipients.

The active compounds or the pharmaceutical preparations can be administered locally, orally, parenterally, intraperitoneally and/or rectally, preferably orally or parenterally, especially intravenously or intramuscularly.

In general it has proved advantageous both in human medicine and in veterinary medicine to administer the active compound or compounds according to the invention in total amounts of about 0.5 to about 500, preferably 4 to 100, mg/kg body weight every 24 hours, optionally in the form of several individual administrations, in order to achieve the best results. An individual administration contains the active compound or the active compounds according to the invention preferably in amounts of about 1 to about 250, especially 3 to 60, mg/kg of body weight. However, it can be necessary to deviate from the dose mentioned and in particular to do so as a function of the nature and body weight of the subject to be treated, the nature and the severity of the illness, the nature of the preparation and of the administration of the medicine, and the time or interval over which the administration takes place.

Thus it can suffice in some cases to manage with less than the abovementioned amount of active compound whilst in other cases the abovementioned amount of active compound must be exceeded. The particular required optimum dosage and the type of administration of the active compounds can easily be decided by anyone skilled in the art, on the basis of his expert knowledge.

METHODS

The methods used for the cleavage of DNA with restriction enzymes, for filling in 5′-protruding ends with dNTP in the presence of DNA polymerase I (Klenow fragment), for digestion with mung bean nuclease, gelelectrophoresis of DNA, isolation of DNA fragments, ligation of DNA fragments, for the transformation of E. coli and for colony hybridization were the standard methods as described by Maniatis et al., Molecular Cloning, Cold Spring Harbor (1982), taking account of the manufacturers' information (restriction enzymes from Boehringer Mannheim (Mannhelm), Biolabs (Schwalbach), Pharmacia (Freiburg); mung bean nuclease, Pharmacia, and competent E. coli cells, BRL, Eggenstein).

Chemical Synthesis of the Oligonucleotides

The oligonucleotides were synthesized in a Pharmacia Gene Assembler ™ using established phosphoramidite chemistry (β-cyanoethyl N,N-diisopropylphosphoramidite) and purified by denaturating polyacrylamide gel electrophoresis.

DNA Sequencing

To verify the DNA sequence of the individual gene constructions, double-stranded DNA was directly sequenced by the method of Chen & Seeburg (DNA, 4, 165, 1985) in both strands in each case.

Yeast Transformation 100 ml of a cell suspension of the yeast strain SC106 (MAT-alpha, hom3, ga12, his6, ura3; strain S2207A, Yeast Genetics Stock Center, University of California, Berkeley, Calif. 94720, U.S.A.) with a cell concentration of $2 \times 10^7$ per ml were spun down; the cell sediment was washed once with 5 ml of TE buffer (10 mM Tris×HCl, pH 7.5, 1 mM EDTA) and then with 5 ml of LiA buffer (0.1M lithium acetate in TE buffer). The cells were then suspended in 1 ml of LiA buffer and incubated at 30° C. for 1 hour. The competent cells obtained in this way could be stored at 4° C. for 1 day. The transformation was carried out in the following way:

10 μl of the plasmid solution (1–5 μg of DNA) and 15 μl of a carrier DNA (denatured DNA from herring sperm, 3 mg/ml) were added to 0.1 ml of cell suspension. Incubation at 30° C. for 30 minutes was followed by addition of 0.7 ml of polypropylene glycol (40% polypropylene glycol 3350 in LiA buffer) and then by further incubation at 30° C. for 60 minutes. The cells were then subjected to a heat shock (42° C., 5 minutes) and subsequently spun down in an Eppendorf microfuge for 4 seconds. The cell pellet was washed twice with 0.5 ml of TE buffer each time, and the cells were then suspended in 0.1 ml of TE buffer and plated out on a selective nutrient medium. Transformants were obtained after 3 days.

Growth of Transformants and Analysis of Secretion Products

Transformants were cultivated in SD medium (0.67% yeast nitrogen base without amino acids, 2% D-glucose) supplemented with threonine, methionine and histidine (20 mg/liter each) at 30° C. After an adequate cell density had been reached, the cells were spun down, and the trypsin- or elastase-inhibiting activity in the culture supernatant was measured.

Polyacrylamide Gel Electrophoresis

Proteins were normally detected by SDS polyacrylamide gel electrophoresis (Laemmli, Nature, 277, 680, 1970) and staining with Coomassie brilliant blue.

Amino Acid Analysis

About 1 nmol of protein was incubated in the presence of 200 μl of 6M HCl, 0.05% β-mercaptoethanol at 110° C. under vacuum for 22 hours. The hydrolysates were dried, dissolved in 150 μl of 0.2M sodium citrate buffer, pH 2.2, and filtered. Amino acid analysis was carried out in a Biotronic LC 5000 amino acid analyser with fluorescence detector and Shimadzu C-R2AX integrator. The amino acids were quantified after reaction with phthalaldehyde in accordance with the literature (Benson & Hare, Proc. Natl. Acad. Sci., USA, 72, 619 (1975)).

Amino Acid Sequencing

1–2 nmol of protein dissolved in 30 μl of trifluoroacetic acid were applied to Polybrene-treated glass fibre filters and sequenced in a gas-phase sequenator (Applied Biosystems) by the method of Hewick et al., J. Biol. Chem., 256, 7990 (1981). Phenylthiohydantoin derivatives were separated and analyzed with the aid of a cyano HPLC column (DuPont) as described by Beyreuther et al., Modern Methods in Protein Chemistry, 303–325, Walter de Gruyter, Berlin (1983), using a Waters HPLC system.

Trypsin Inhibition Assay

The trypsin activity was determined using the method of Geiger & Fritz, Methods of Enzymatic Analysis, Vol. V, 3rd ed., Bergmeyer (ed.), Verlag Chemie, Weinheim (1984), p. 121 with benzoyl-L-arginine p-nitroanilide as substrate. The liberated p-nitroaniline was measured in a spectrophotometer at 405 nm. Enzyme and inhibitor were preincubated for 15 minutes before addition of the substrate.

Elastase Inhibition Assay

Human leukocyte elastase was obtained from Elastin Products Company Inc., P.O. Box 147, Pacific, Miss. 63069/U.S.A. The substrate used was MeOSuc-Ala-Ala-Pro-Val-pNA (Bachem, Bubendorf, Switzerland). The assay conditions are indicated in Table 1. In general, the inhibitor samples were diluted with assay buffer, enzyme was added and the mixture was then preincubated. The reaction was started by addition of substrate (dissolved in DSMO in a concentration of 0.1M and adjusted to the concentration of the stock solution with buffer), and the liberation of p-nitroaniline from the substrate was continuously followed at 405 nm. 100% values were determined in corresponding assays without inhibitors. The inhibition (in percent) was calculated from the following equation.

$$\% \text{ Inhibition} = 100 \times \left[ 1 - \frac{\Delta OD \text{ in the presence of inhibitor}}{\Delta OD \text{ in the absence of inhibitor}} \right]$$

TABLE 1

| Conditions for the elastase inhibition assay (Nakajima et al., J. Biol. Chem., 254, 4027, 1979). | |
|---|---|
| Buffer | 0.2M Tris/HCl, pH 8.0 + 0.1% Tween 80 |
| Total volume after addition of substrate | 0.65 ml |
| Enzyme quantity/assay | 50 ng |
| Preincubation time at room temperature | 30 minutes |
| Substrate | MeO—Suc—Ala—Ala—Pro—Val—pNA |
| Stock solution | 0.065M |
| Quantity/assay | 0.1 ml |
| Assay temperature | 30° C. |

EXAMPLE 1

Construction of the Bikunin Gene Variants and Expression in *E. coli*

The individual bikunin gene variants are based on the natural mRNA on the one hand and on synthetic genes of the individual domains, or parts thereof on the other hand. The cDNA clones were obtained from suitable cDNA banks by hybridization with oligonucleotide probes (Kaumeyer et al., Nucleic Acids Res.,14, 7839–7849, 1986) or by screening with antibodies against human inter-α-trypsin inhibitor (Schreitmüller et al., Biol. Chem. Hoppe-Seyler, 368, 963–970, 1987). The synthetic genes (1st domain) or gene segments (2nd domain) were obtained as follows:

Construction of the de[$^{1-17,78-147}$]-Met$^{18}$-Xaa$^{36}$-Xaa$^{38}$-bikunin gene with, for example, Xaa=Ile, Leu, Met or Val The genes for the first domain (de[$^{1-17,78-147}$]-Met$^{18}$-bikunin) and its variants (de[$^{1-17,78-147}$]-Met$^{18}$-Xaa$^{36}$-Xaa$^{38}$-bikunin with, for example, Xaa=Ile, Leu, Met or Val) were constructed from two modules which were generated by complete synthesis and which can be removed, singly or together, from these genes by cleavage with the suitable combination of restriction nucleases NcoI, Asp718 and SalI. The construction facilitates the manipulation of the genes in various vector systems and, via the internal Asp718 restriction cleavage site, the replacement of the modules for the preparation of the variants (FIG. 2).

Module 1 embraces oligonucleotides 1–6 and module 2 oligonucleotides 7–12. The construction of Xaa$^{36}$-Xaa$^{38}$- variants requires merely the replacement of module 1. To construct the module 1 variants, oligonucleotides 2,3,5 and 6 were replaced where necessary by oligonucleotide variants in which the codon for methionine (ATG) had been replaced by one for isoleucine (ATC), leucine (CTG) or valine (GTT) or the complementary sequence thereof in the opposite strand. The N-terminal sequence V-T-K is part of the natural N-terminal peptide. The only foreign amino acid is the start methionine, whose elimination can be achieved on direct expression of the gene in E.coli in vivo.

The cloning strategy is outlined in FIG. 3. Plasmid pTZ18NCO was prepared by cleavage of pTZ18R (Pharmacia) with EcoRI, treatment with mung bean nuclease, ligation with the palindromic sequence 5'-ACCATGGT-3' and transformation into E.coli DH5. The construction was verified by sequence analysis.

The plasmids pTZMOD1 and pTZMOD1XX (XX=IL, LM, MM, LT, VL) were characterized by sequencing after cleavage of plasmid pTZ18NCO with NcoI and Asp718, ligation of the linearized plasmid with the oligonucleotides 1–6 (module 1, FIG. 2) or the corresponding oligonucleotide variants, which had been phosphorylated with polynucleotide kinase, transformation into E.coli DH5, colony hybridization with radioactively labelled oligonucleotide 4 and isolation of the plasmid DNA.

Plasmid pTZKUN1 was isolated after cleavage of plasmid pTZMOD1 with Asp 718 and SalI, ligation of the linearized plasmid with oligonucleotides 7–12 (module 2, FIG. 2 ) which had been phosphorylated with polynucleotide kinase, transformation into E.coli DH5 and colony hybridization with radioactively labelled oligonucleotide 11, and characterized by sequencing of the plasmid DNA.

To construct the plasmids pTZKUN1XX (XX=IL, LM, MM, LL, VL) the fragment of module 2 removed from pTZKUN1 with Asp718 and SalI was used, in place of the individual oligonucleotides 7–12 of this module, and the procedure for the construction was otherwise analogous to those already described.

Construction of de[$^{1-17}$]-Met$^{18}$-Xaa$^{36}$-Xaa$^{38}$-bikunin genes Bikunin genes of the de[$^{1-17}$]-Met$^{18}$-Xaa$^{36}$-Xaa$^{38}$-bikunin type are double-headed variants with amino acid replacements only in the first domain. They were obtained by condensation of the synthetic gene of the first domain or of its variants with a natural gene fragment of the second domain. The cloning strategy is described in FIG. 4.

Plasmid pTZBIK was obtained from the cDNA of an α$_1$-microglobulin-bikunin clone (pTZ18MB1) which was cloned in the plasmid pTZ18R by cleavage with the restriction nuclease Sau3A. This generated fragment A (FIG. 4), which was isolated by gel electrophoresis. The fragment possesses the almost complete sequence of the bikunin gene without the α$_1$-microglobulin-encoding portion and a small part of the gene segment for the N-terminal peptide of bikunin. The fragment ends were selectively filled in with dATP and dGTP in the presence of Klenow enzyme, made blunt-ended with mung bean nuclease and cloned into plasmid pTZ19R (Pharmacia) which had been linearized with HindIII and likewise made blunt-ended with mung bean nuclease. Transformation into E.coli DH5 was carried out. The plasmid DNA of the resulting clones was verified by sequence analysis.

The plasmids pTZBIK1 and pTZBIK1XX (XX=IL, LM, MM, LL, VL) were generated by replacing the natural gene segment for domain 1 of the bikunin gene by the appropriate synthetic gene segment or one of its variants. The fragment C of the pTZBIK DNA was isolated after cleavage with SphI and PstI and contains the complete cDNA sequence of bikunin with the exception of the gene segment for almost all of domain 1 and was ligated into correspondingly cleaved plasmids pTZKUN1 and pTZKUN1XX (XX=IL, LM, MM, LL, VL) (see FIG. 3) and cloned into E.coli DH5. The plasmid DNA of the resulting clones was characterized by sequence analysis.

Construction of the de[$^{1-79}$]-Xaa$^{92}$-Xaa$^{94}$-bikunin gene with Xaa=Ile, Leu, Met, Val, Phe The gene of the second domain (de[$^{1-79}$]-bikunin) was obtained by truncating the bikunin (FIG. 5). Its variants (de[$^{1-79}$]-Xaa$^{92}$-Xaa$^{94}$-bikunin) were prepared by replacement of an ApaI/XmnI restriction fragment of domain 2 (module 3) by suitable combinations of oligonucleotides A-D or their variants (FIG. 6) as shown in FIG. 7.

Plasmid pTZKUN2 (FIG. 5 ) was obtained by ligation of fragment A, which was generated by treatment of pTZBIK1 DNA with the restriction nucleases HindIII and BspMI and made blunt-ended at the fragment ends with mung bean nuclease, with vector pTZ19R (Pharmacia) which had been cleaved with XcyI and likewise treated with mung bean nuclease, after transformation of E.coli DH5 cells. The plasmid DNA of individual clones was characterized by sequence analysis.

The plasmids pTZKUN2XX (XX=IL, LL, VL and LF) were obtained by replacement of an ApaI/XmnI fragment of pTZKUN2 by the appropriate oligonucleotides of module 3 (see FIG. 6). The vector fragment was isolated after cleavage with the said restriction nucleases and dephosphorylation of the 5' ends with calf intestinal alkaline phosphatase. After ligation with the oligonucleotides of module 3 which had been phosphorylated with polynucleotide kinase, and transformation into E.coli DH5, the plasmid DNA of individual clones was characterized by mapping and, finally, sequence analysis (FIG. 7).

Construction of de[$^{1-17}$-Met$^{18}$-Xaa$^{36}$-Xaa$^{38}$-Xaa$^{92}$-Xaa$^{94}$-]bikunin genes Bikunin gene variants with replacements in both domains were generated from bikunin gene variants with a variant domain 1 (pTZBIK1XX; FIG. 4) by replacing a gene segment of the natural domain 2 by a corresponding segment of the gene variants of domain 2 (FIG. 7) in the way shown in FIG. 8.

Cleavage of plasmid pTZBIXX by the restriction nucleases EcoRI and ApaI, dephosphorylation of the 5' ends of the DNA fragments with calf intestinal alkaline phosphatase and isolation of the vector fragment were followed by ligation with the likewise isolated EcoRI/ApaI fragment from pTZKUN2XX and cloning into E.coli DH5. The plasmids of individual clones were characterized by sequence analysis.

Construction of the de[$^{1-17,82-147}$]-Met$^{18}$-Xaa$^{36}$-Xaa$^{38}$-bikunin gene Genes of the first domain with additional C-terminal extension by the amino acid sequence T-V-A-A (de[$^{1-17,82-147}$]-Met$^{18}$-Xaa$^{36}$-Xaa$^{38}$-bikunin) were obtained from the plasmids pTZBIK1XX of the appropriate bikunin variants after replacement of the second domain by the oligonucleotides a (5'-CTGTGGCGGCCTGAG-3') and b (5'-AATTCT-CAGGCCGCC-3') (FIG. 9). For this purpose, pTZBIK1XX was cleaved with BspMI and EcoRI, the 5' ends of the DNA fragments were dephosphorylated with calf intestinal alkaline phosphatase, and the vector fragment was isolated and ligated in the presence of the oligonucleotides. After transformation of E.coli DH5, the plasmids pTZKUN1XXc of individual clones were verified by sequence analysis.

Expression of Bikunin Variants

It was possible for some of the bikunin gene variants described to be expressed both in the cloning vector itself and after recloning into various expression vectors such as, for example, pJLA502 (Schauder et al., Gene, 52, 279–283, 1987) pEX3 (Stanley & Luzio, EMBO J. 3, 1429–1434, 1984) and pEX3407 (Kocken et al., FEBS Lett., 236, 132–134, 1988). For example, NcoI/SalI and NcoI/EcoRI fragments can be isolated from the plasmids pTZKUN1XX and pTZBIK1XX2XX respectively (FIGS. 3 and 8) and directly ligated into the vector pJLA502 which has been correspondingly cut and treated with calf intestinal alkaline phosphatase. Alternatively, fragments from the plasmids pTZBIK1XX (NcoI/EcoRI fragment, FIG. 4), pTZBIK1XX2XX (NcoI/EcoRI fragment, FIG. 8), pTZKUN1XX (NcoI/HindIII fragment, FIG. 3) can be isolated, made blunt-ended with mung bean nuclease and ligated into the vectors pEX3 or pEX3407.

Fragments of the plasmid pTZKUN2XX (FIG. 7) can be generated by cleavage with EcoRI, treatment with mung bean nuclease and subsequent cleavage with BamHI and ligated into the pEX vectors. DNA of the pEX vectors can for this purpose be either cut with SalI and treated with mung bean nuclease or, as in the last-mentioned construction, cleaved with PstI, treated with mung bean nuclease and subsequently cleaved with BamHI. Transformants of E.coli pop2136 (Vidal-Ingliardi & Raibaud, Nucleic Acids Res., 13, 1163, 1985) allow temperature-dependent control of gene expression. The fusion proteins which are produced in every case are linked via an acid-labile Asp-Pro peptide linkage to the protein to be expressed. Removal of the fusion protein portion, purification and renaturation of the bikunin portion resulted in inhibitor variants of the de[$^{1-17}$]-Pro$^{18}$-bikunin, de[$^{1-17,78-147}$]-Pro$^{18}$-bikunin and de[$^{1-78}$]-Pro$^{79}$-bikunin types. The bikunin part can also be cleaved from the fusion partner by use of the sequence Pro$^{20}$-Lys$^{21}$-Lys$^{22}$ which is particularly labile to proteolysis (with trypsin). It was possible for single-headed variants to be expressed particularly well in secretory expression systems.

The expression products were detected either by gel electrophoresis (for example for determination of fusion proteins) or in standard enzyme inhibition assays (after elimination of the fusion partner, purification and renaturation of the bikunin part).

The results which were obtained show that, for example, de[$^{1-17}$]-Met-18-Leu-36-Leu-38-bikunin, de[$^{1-17}$]-Met-18-Leu-36-Leu-38-Leu-92-Leu-94-bikunin and de[$^{1-17}$]-Met-18-Leu-92-Leu-94-bikunin, prepared in the manner described by expression in E.coli, have a potent protease inhibiting action.

EXAMPLE 2

Expression of Leu-36-Leu-38-bikunin

Cloning of the gene pCY17, a vector derived from pBR322, which contains the MAT-alpha-1 structural gene (Kurjan and Herskowitz, Cell, 30, 933, 1982) was obtained from Herskowitz, University of California. pMT15 is a yeast-E.coli shuttle vector (FIG. 10). It carries Amp$^R$, bla and URA3 gene segments which act as selectable markers for E.coli and yeast. pMT15 additionally has the ColE1 origin of pBR322 and a segment of the B form of the 2μ plasmid, so that the plasmid can undergo stable replication both in E.coli and in yeast. It additionally carries the MAT1-alpha promoter and the coding sequence of the N-terminal pre-pro-sequence of the alpha factor precursor protein as EcoRI-HindIII fragment which had been obtained from the plasmid pCY17. This fragment is followed at the 3' end by a 115 bp HindIII-BamHI fragment which codes for the 34 N-terminal amino acids of pre-invertase (Das et al., Mol. Gen. Genet., 218, p. 240, 1989). Finally, pMT15 contained at the 3' end of the BamHI cleavage site a 160 bp fragment of a yeast transcription terminator which had been obtained from the yeast URA3 gene (Yarger et al., Mol. Cell. Biol., 8, 1095, 1986).

The 235 bp PstI-HindIII fragment from pMT15 which carries the coding region of the alpha-factor pre-pro-leader sequence was cloned into the vector M13mp18 and subjected to directed mutagenesis using the mutagenic oligonucleotide 5'-GAA GAA GGG GTA TTG GAT AAA AGA-3'. The result of the mutagenesis was that the serine codon at position 81 in the alpha-factor pre-pro-sequence was changed from TCT to AGC, which generated a HindIII restriction cleavage site. The 213 bp PstI-HindIII fragment (FIG. 11) prepared thereby was used to replace the 235 bp PstI-HindIII fragment in pMT15. The plasmid modified in this way was called pS600; it carries the coding sequence for Lys-Arg in place of Lys-Arg-Glu-Ala-Glu-Ala as processing site (FIG. 12).

Construction of the Leu-36-Leu-38-bikunin gene: a 540 bp Sau3AI fragment from the plasmid PIM1 (Das and Lehman, J. Cell. Biochem., 2B, 284, 1988) which carries the coding sequence of bikunin (FIG. 13) was cloned into M13mp19 and subjected to site-directed mutagenesis in order to transform Met-36 into Leu-36 and Met-38 into Leu-38. The mutagenesis was carried out by the method of Sayers et al. (Nucl. Acids. Res., 16, 79, (1988)). Additionally prepared was a double-stranded DNA fragment of the following sequence:

```
5'...AGC TTG GAT AAA AGA GCT GTG CTA CCC CAA
3'-      AC  CTA TTT TCT CGA CAC GAT GGG GTT

GAA GAG GAA G.......... 3'
CTT CTC CTT CCT AG ...5'
```

The DNA fragment was phosphorylated by standard processes. The DNA fragment obtained in this way was inserted together with the mutated bikunin sequence into the 8.2 bp pS600 plasmid which had been digested with HindIII and BamHI. The oligomer reconstituted both the 3' end of the pre-pro-alpha-factor sequence and the 5' end of the bikunin sequence. The new plasmid pLLB3638 obtained in this way accordingly contains the coding region for the pre-pro-alpha-factor sequence with Lys-Arg as processing site fused to the Leu-36-Leu-38-bikunin sequence. The DNA and the corresponding amino acid sequence at the fusion site of pre-pro-alpha-factor-Leu-36-Leu-38-bikunin in pLLB3638 is depicted in FIG. 14.

Expression, secretion and detection of Leu-36-Leu-38-bikunin having inhibitory activity Yeast strain SC106 (MATα, hom3, gal2, his6, ura3) was transformed with pLLB3638 in accordance with the methods described above; URA3+ cells were isolated and cultivated; the culture supernatant was tested for elastase-inhibitory activity. It was shown in control tests that SC106 cells transformed with pS600 produced no elastase-inhibitory activity in the culture medium.

The results which were obtained showed that the Leu-36-Leu-38-bikunin gene expressed in Saccharomyces cerevisiae led to the formation of two protein species in the culture medium with the following properties: (a) active trypsin inhibitors, (b) molecular weight of 20 k and 17 k according to electrophoresis in SDS polyacrylamide gels, (c) of each protein species about 60% showed the N-terminal sequence of bikunin and about 40% showed the sequence of de(Ala-1)-bikunin.

EXAMPLE 3

Expression of Leu-92-Leu-94-bikunin

Cloning of the gene

The 540 bp Sau3AI fragment of the pIM1 DNA (Das and Lehman, J. Cell. Biochem. 12 B, 284, 1988) with the coding sequence of bikunin (FIG. 13) was cloned into the plasmid M13mp19 and subjected to directed mutagenesis in order to change Arg-92 into Leu-92 and Phe-94 into Leu-94. The fragment mutated in this way was cloned into the plasmid pS600 analogous to Example 1. The DNA sequence and the corresponding amino acid sequence at the fusion site of the pre-pro-alpha-factor-Leu-92-Leu-94-bikunin gene in the expression vector pLLB9294 is depicted in FIG. 15.

Expression, secretion and detection of Leu-92-Leu-94-bikunin having inhibitory activity SC106 was transformed with pLLB9294 in accordance with the methods described above; URA3+ cells were isolated and cultivated; the culture supernatant was tested for elastase-inhibitory activity. It was shown in control tests that SC106 cells transformed with pS600 produced no elastase-inhibitory activity in the culture medium.

The results which were obtained showed that the Leu-92-Leu-94-bikunin gene expressed in Saccharomyces cerevisiae led to the formation of two protein species in the culture medium with the following properties: (a) active elastase inhibitors, (b) molecular weight of 20 k and 17 k according to electrophoresis in SDS polyacrylamide gels, (c) of each protein species about 60% showed the N-terminal sequence of bikunin and about 40% showed the sequence of de(Ala-1)-bikunin.

EXAMPLE 4

Expression of Leu-36-Leu-38-Leu-92-Leu-94-bikunin

Cloning of the gene

The 540 bp Sau3AI fragment of the pIM1 DNA (Das and Lehman, J. Cell. Biochem. 12 B, 284, 1988) with the coding sequence of bikunin (FIG. 13) was cloned into the plasmid M13mp19 and subjected to directed mutagenesis in order to change Met-36 into Leu-36, Met-38 into Leu-38, Arg-92 into Leu-92 and Phe-94 into Leu-94. The fragment mutated in this way was cloned into the plasmid pS600 analogous to Example 1. The DNA sequence and the corresponding amino acid sequence at the fusion site of the Pre-pro-alpha-factor-Leu-36-Leu-38-Leu-92-Leu-94-bikunin gene in the expression vector p4LB is depicted in FIG. 16.

Expression, secretion and detection of Leu-36-Leu-38-Leu-92-Leu-94-bikunin having inhibitory activity SC106 was transformed with p4LB in accordance with the methods described above; URA3+ cells were isolated and cultivated; the culture supernatant was tested for elastase-inhibitory activity. It was shown in control tests that SC106 cells transformed with pS600 produced no elastase inhibitory activity in the culture medium.

The results which were obtained showed that the Leu-36-Leu-38-Leu-92-Leu-94-bikunin gene expressed in Saccharomyces cerevisiae led to the formation of two protein species in the culture medium with the following properties: (a) active elastase inhibitors, (b) molecular weight of 20 k and 17 k according to electrophoresis in SDS polyacrylamide gels, (c) of each protein species about 60% showed the N-terminal sequence of bikunin and about 40% showed the sequence of de(Ala-1)-bikunin.

EXAMPLE 5

Expression of de(1-21)-Leu-36-Leu-38-bikunin

Cloning of the gene

A 480 bp PvuII fragment of the pIM1 DNA (Das and Lehmann, J. Cell. Biochem. 12 B, 284, 1988), which carries the coding region of de(1-21)-bikunin (FIG. 13) was cloned into the plasmid M13mp19 and subjected to directed mutagenesis in order to change Met-36 into Leu-36 and Met-38 into Leu-38. The mutagenesis was carried out by the method of Sayers et al. (Nucl. Acids. Res., 16, 791, 1988). Additionally prepared was a double-stranded DNA fragment of the following sequence:

```
5'-AGC TTG GAT AAA AGA AAA GAA GAT TCC TGC CAG-3'
    AC  CTA TTT TCT TTT CTT CTA AGG ACG GTC-5'
```

The DNA fragment was phosphorylated by standard processes. The DNA fragment obtained in this way was inserted together with the mutated bikunin sequence into the 8.2 bp pS600 plasmid which had been digested with HindIII and BamHI. The oligomer reconstituted both the 3' end of the pre-pro-alpha-factor sequence and the 5' end of the bikunin sequence. The new plasmid pDLLB-121 obtained in this way accordingly contains the coding region for the pre-pro-alpha-factor sequence with Lys-Arg as processing site fused to the de(1-21)-Leu-36-Leu-38-bikunin sequence. The DNA and the corresponding amino acid sequence at the fusion site of pre-pro-alpha-factor-Leu-36-Leu-38-bikunin in pDLLB-121 is depicted in FIG. 17.

Expression, secretion and detection of de(1-21)-Leu-36-Leu-38-bikunin having inhibitory activity SC106 was transformed with pDLLB-121 in accordance with the methods described above; URA3+ cells were isolated and cultivated; the culture supernatant was tested for elastase-inhibitory activity. It was shown in control tests that SC106 cells transformed with pS600 produced no elastase-inhibitory activity in the culture medium.

The results which were obtained showed that the de(1-21)-Leu-36-Leu-38-bikunin gene expressed in Saccharomyces cerevisiae led to the formation of a protein in the culture medium with the following properties: (a) active trypsin inhibitor, (b) molecular weight of 17 k and 15 k according to electrophoresis in SDS polyacrylamide gels, (c) the protein showed the N-terminal sequence Lys-Glu-Asp-Ser-Cys of de(1-21)-bikunin.

BRIEF DESCRIPTION OF THE DRAWINGS

FIG. 1 schematically depicts the primary structure of human bikun The N-terminal peptide (pos. 1-21) and domains 1 (pos. 22-77) and 2 (pos. 78-147) can be obtained by cleavage with trypsin. Arrows indicate sequences of those regions which are encoded by different exons, and asterisks indicate the specifically altered residues $P_1$ and $P_2'$ of the reactive centers. Identical amino acid residues in the two inhibitor domains of bikunin are emphasized by vertical lines.

FIG. 2 schematically depicts construction of de[1-17,78-147]-Met[18]-Xaa[36]-Xaa[38]-bikunin variants derived from the oligonucleotide sequence of the basic gene. The residues replaced in the variants are underlined twice. The first codon at the 5' terminus of the genus part of the NcoI recognition sequence CCATGG, and the last nucleotide of the third of three consecutive stop codons (end) at the 3[1] terminus of the gene is part of a SalI recognition sequence GTCGAC. The recognition sequences for the restriction nucleases NcoI, Asp718 and SalI, which limit the individual modules, are underlined once. The oligonucleotides used for gene construction are represented by arrows and are numbered.

M: $\alpha_1$-microglobulin; D1 and D2: domains 1 and 2 of bikunin; N: N-terminal peptide of bikunin; C: C-terminal sequence of bikunin; KUN1: synthetic domain 1 consisting of modules Mod1 and Mod2. Cleavage sites which are lost due to the cloning procedure are registered, but no longer identified, in the resulting plasmid. Fragments B and D—if they were not generated as such—are indicated to improve orientation.

Figure 3:
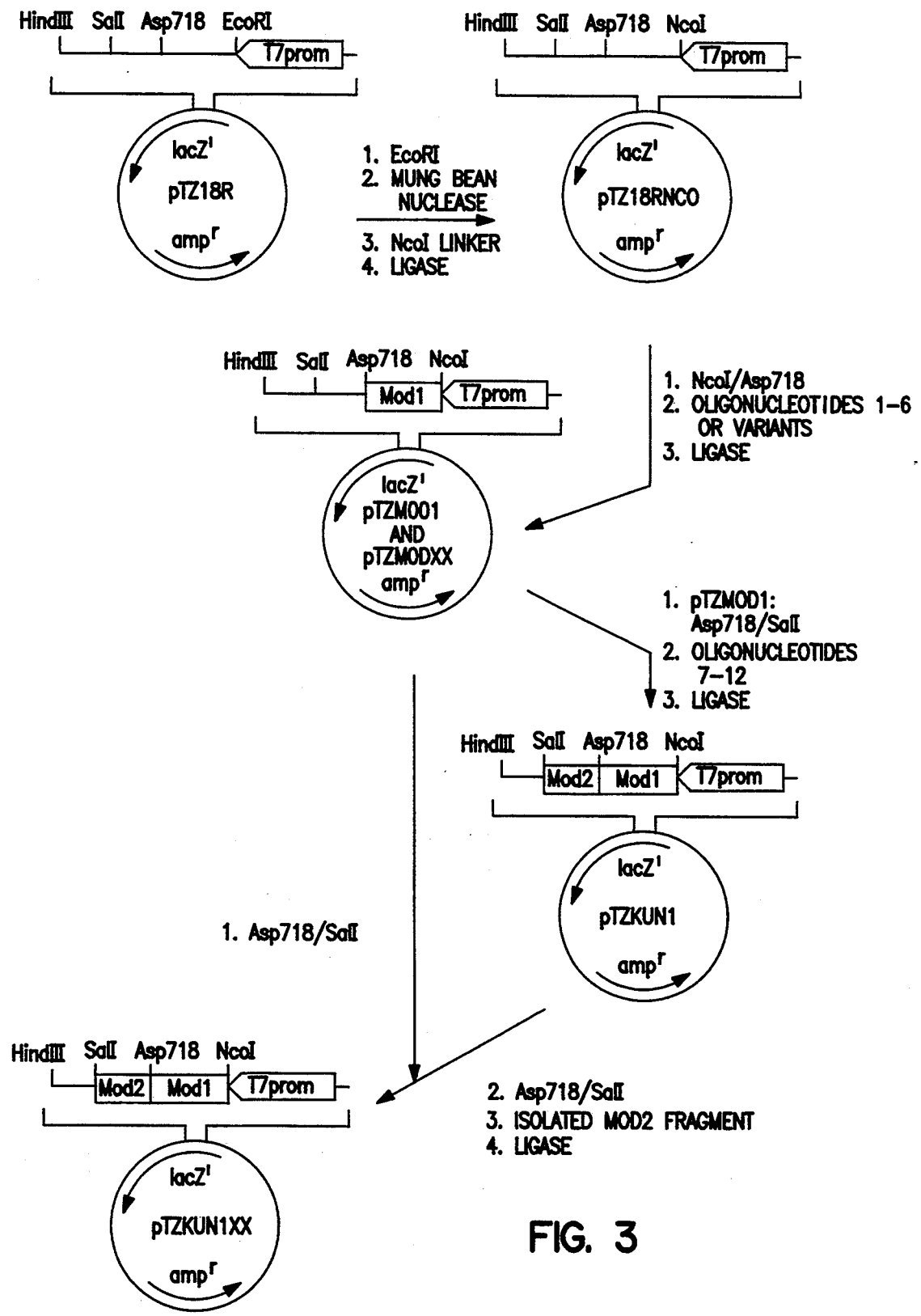
FIG. 3 schematically depicts the cloning of the de[1-17,78-147]-Met[18]-bikunin gene (pTZKUN1) and of the de[1-17,78-147]-Met[18]-Xaa[36]-Xaa[38]-bikunin gene variants (pTZKUN1XX).
Figure 4:
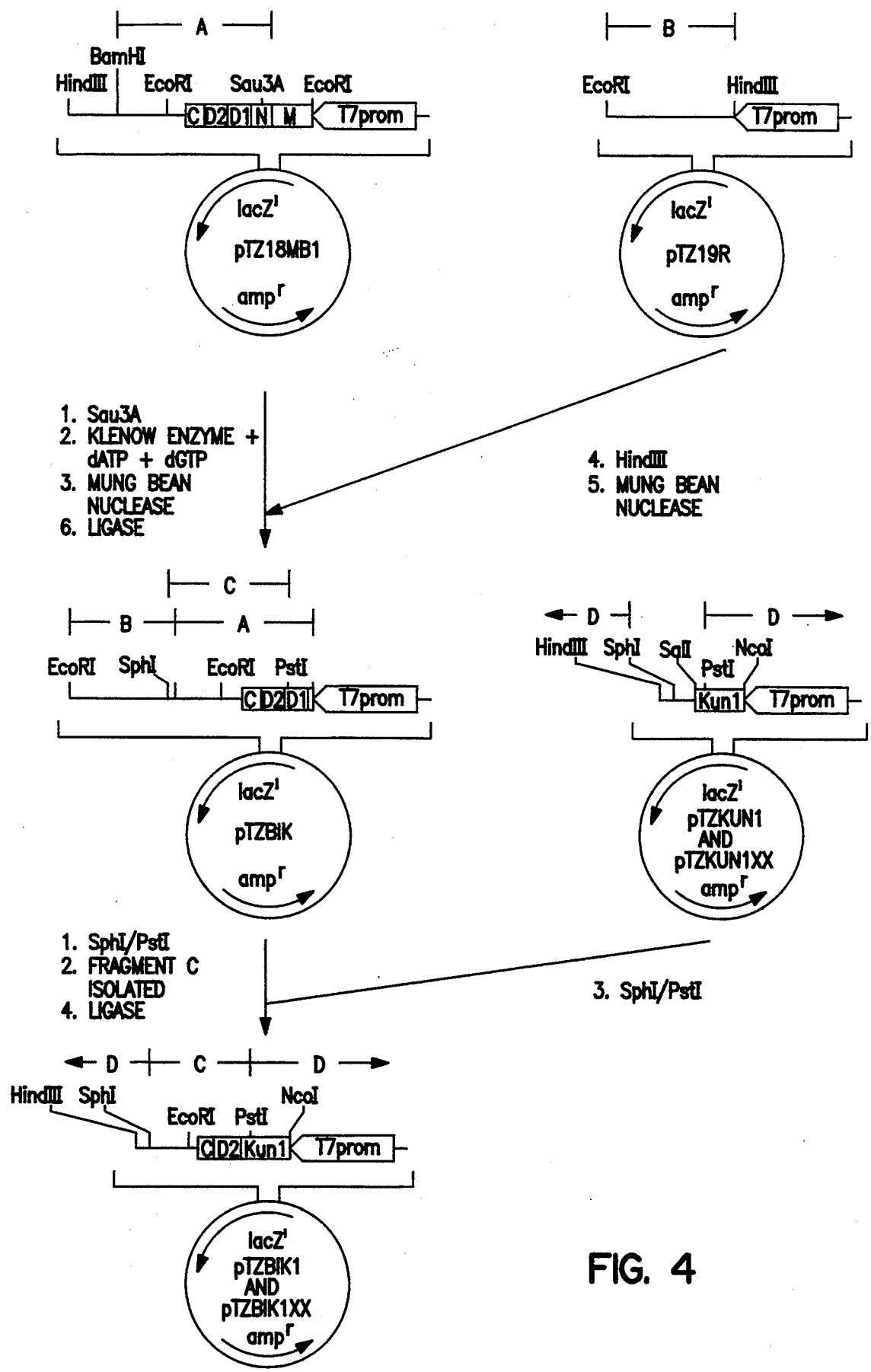
FIG. 4 schematically depicts the cloning of the de[1-17]-bikunin gene (pTZBIK) and of the de[1-17]-Met[18]-bikunin (pTZBIK1) and de[1-17]-Met[18]-Xaa[36]-Xaa[38]-bikunin gene (pTZBIK1XX).
Figure 5:
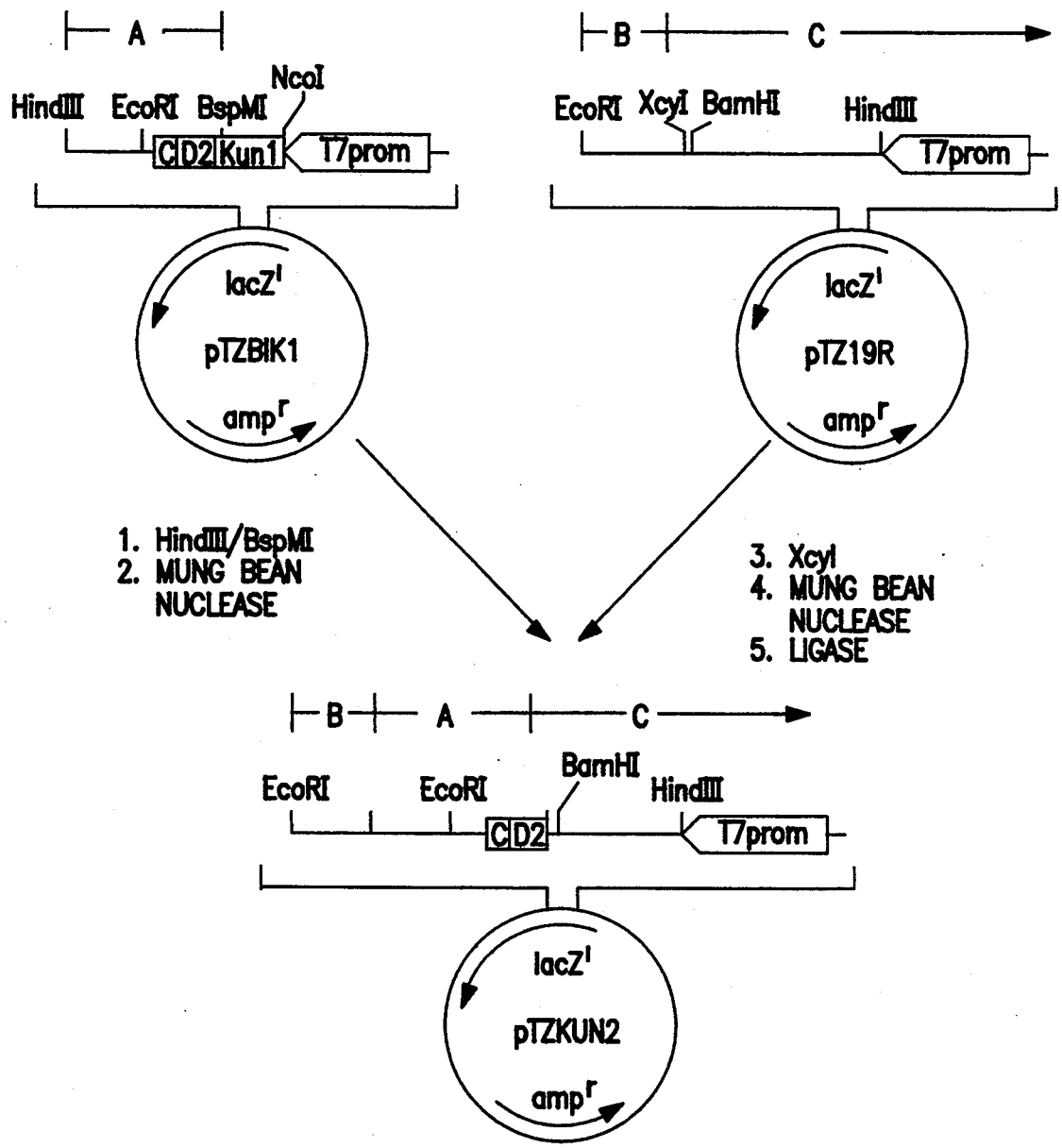

FIG. 5 schematically depicts the cloning of the de[1-79]-bikunin gene (pTZKUN2)

D2: domain 2 of bikunin, C: C-terminal sequence of bikunin; KUN1: synthetic domain 1 consisting of modules Mod1 and Mod2; cleavage sites which are lost due to the cloning procedure are registered in the resulting plasmid without identification. Fragments—even if they were not generated as such—such as, for example, B and C—are indicated to improve orientation.

FIG. 6 schematically depicts the construction of the second domain of bikunin: de[1-79]-Xaa[92]-Xaa[94]-bikunin variants and de[1-17]-Met[18]-Leu[36]-Leu[38]-Leu[92]-Leu[94]-bikunin with Xaa[92]-Xaa[94]=Ile, Leu, Met, Val or Phe.

Shown is the natural bikunin sequence from domain 2 (position 78) and the synthetic oligonucleotides A-D (arrows) in which the codons in positions 92 and 94 of bikunin (underlined twice) in oligonucleotides A and B have been replaced in accordance with the requirements of the individual variants (Ile: ATC; Leu: CTG; Val: GTT; or their complementary sequences in the opposite strand). The recognition sequences for restriction nucleases ApaI (GGGCCC) and XmnI (GAANNNNTTC) are underlined once.

Figure 7:
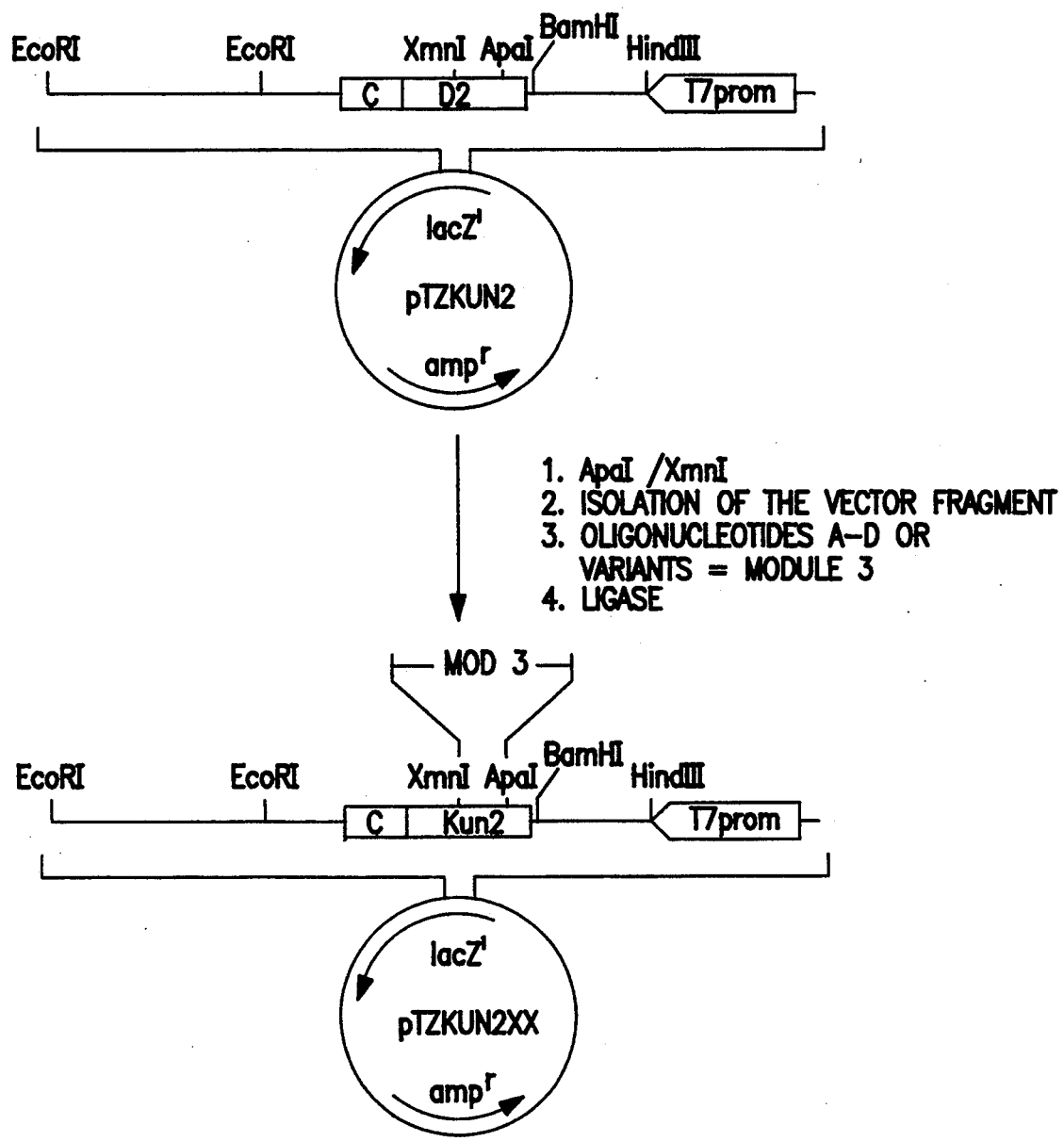

FIG. 7 schematically depicts the cloning of the de[1-79]-Xaa[92]-Xaa[94]-bikunin gene variants with Xaa=Ile, Leu, Met and Val D2: domain 2 of bikunin; KUN2: domain 2 of bikunin after replacement of the natural XmnI/ApaI fragment by the synthetic module 3; C: C-terminal sequence of bikunin.

Figure 8:
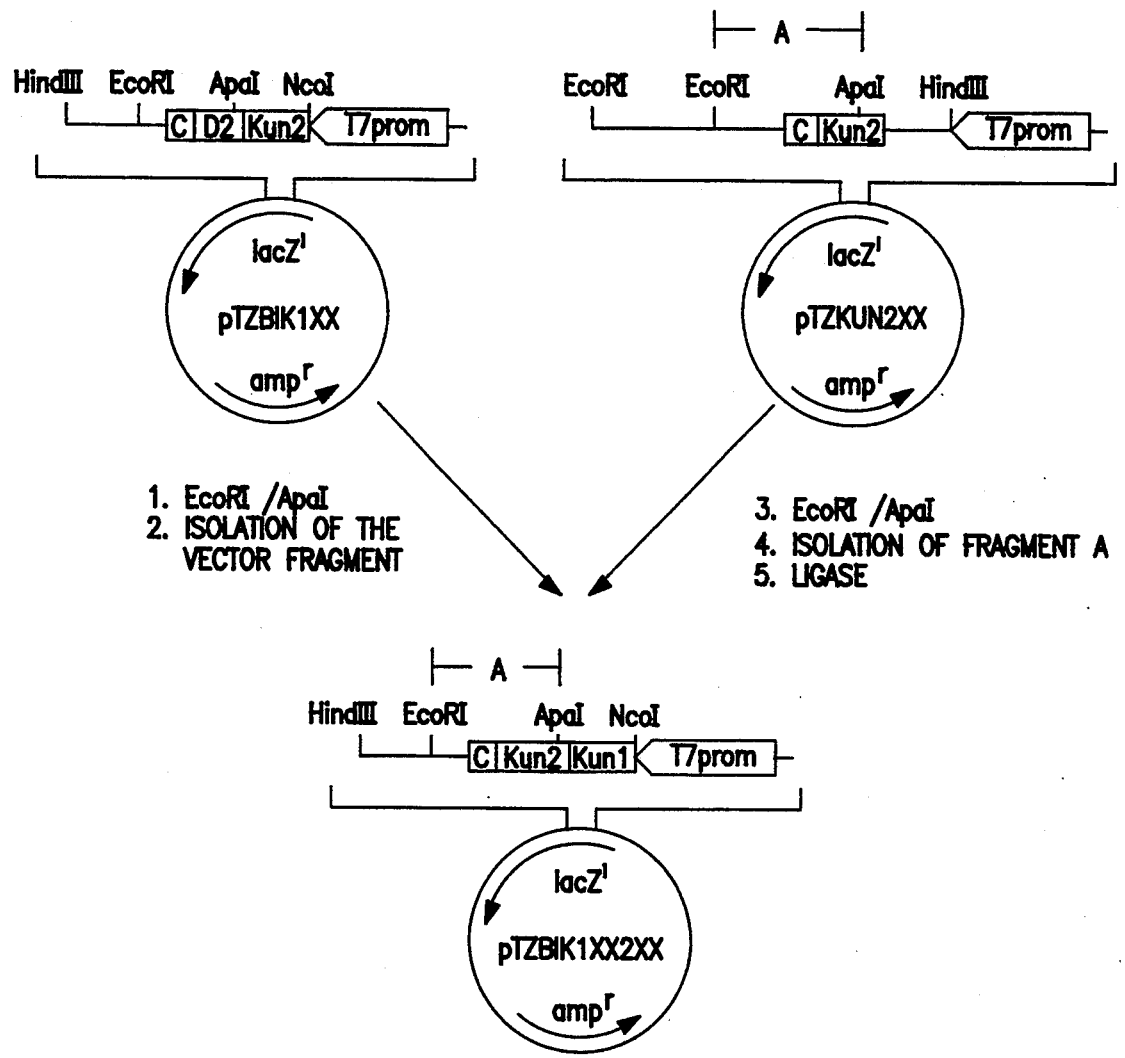

FIG. 8 schematically depicts the cloning of the de[1-17]-Met[18]-Xaa[36]-Xaa[38]-Xaa[92]-Xaa[94]-bikunin gene variants with Xaa=Ile, Leu, Met, Val or Phe.

Figure 9:
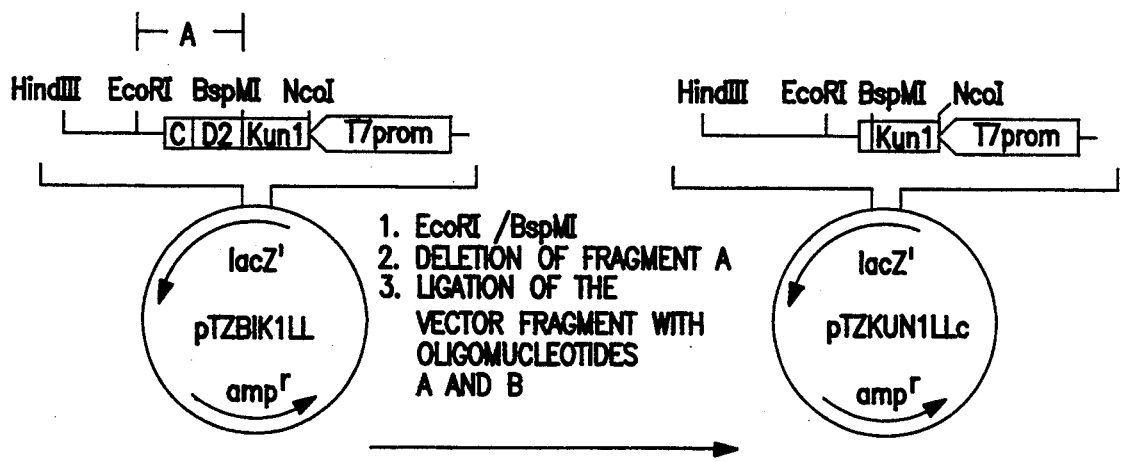

KUN1: synthetic domain 1 consisting of modules 1 and 2; KUN2: domain 2 of bikunin after replacement of the natural XmnI/ApaI fragment by the synthetic module 3; C: C-terminal sequence of bikunin FIG. 9 schematically depicts the cloning of de[1-17,82-147]-Met[18]-Xaa[36]-Xaa[38]-bikunin gene (C-terminal extension of the first domain by the amino acid sequence T-V-A-A). KUN1: synthetic domain 1 consisting of modules 1 and 2; D2: domain of bikunin; C: C-terminal sequence of bikunin; a and b: oligonucleotide linkers (see text).

Figure 10:
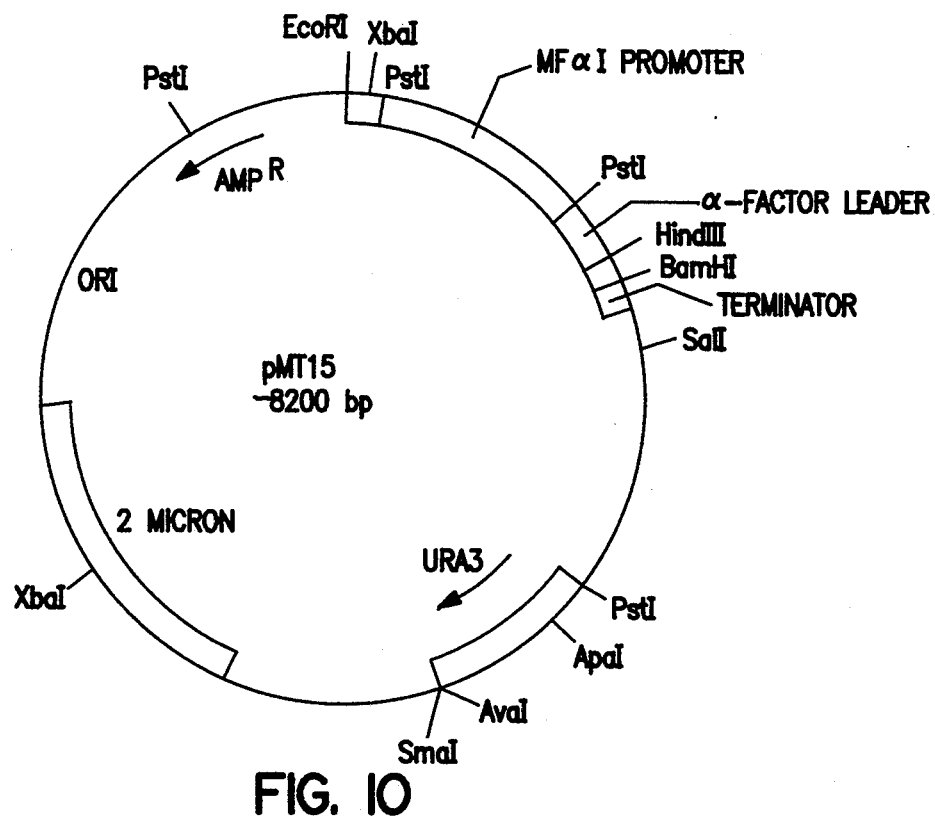

FIG. 10 schematically depicts pMT15, an E.coli-yeast shuttle vector.

Figure 11:
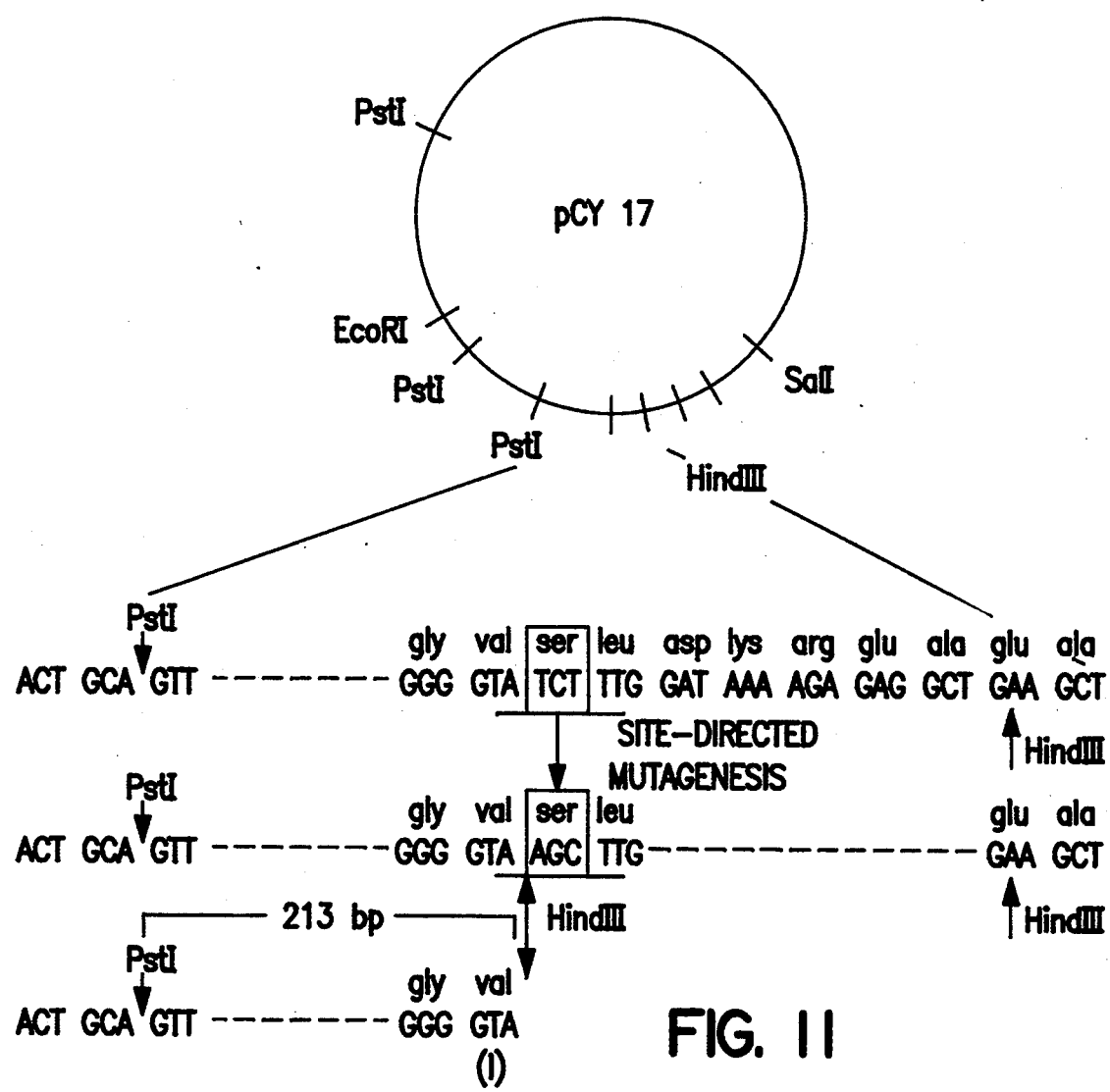

FIG. 11 is a diagram of the site-directed mutagenesis of the alpha-factor leader sequence. The mutagenesis of TCT to AGC facilitates the isolation of a 213 bp PstI-HindIII fragment which is called (I).

Figure 12:
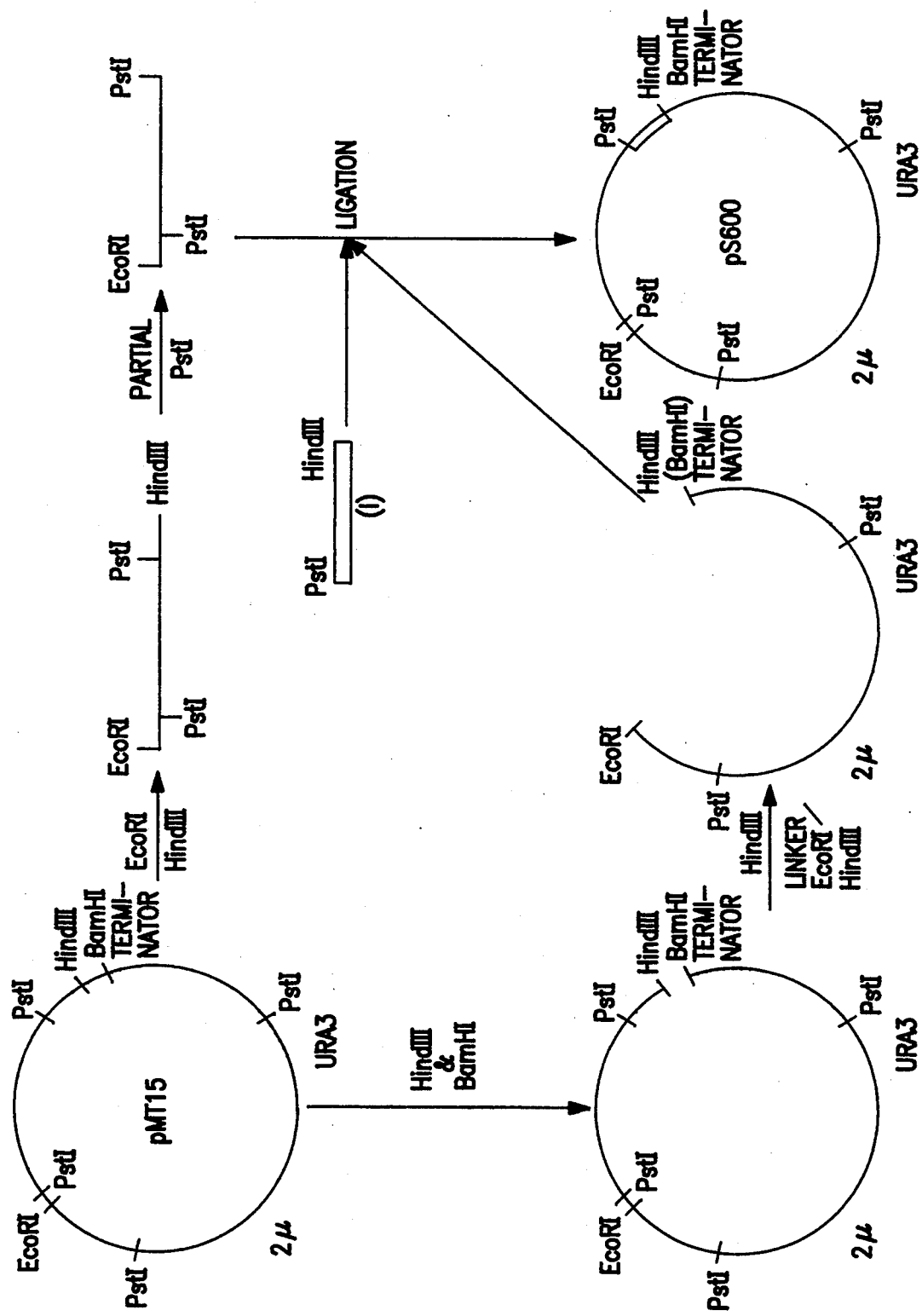

FIG. 12 schematically depicts the construction of a modified yeast-E.coli shuttle vector for the expression/secretion of bikunin using the alpha-factor promoter and the modified alpha-factor leader sequence. The modified alpha-factor leader sequence (called I in FIG. 11) was incorporated as PstI-HindIII gene fragment into the vector pMT15 and there replaced the original alpha-factor leader sequence.

Figure 13:
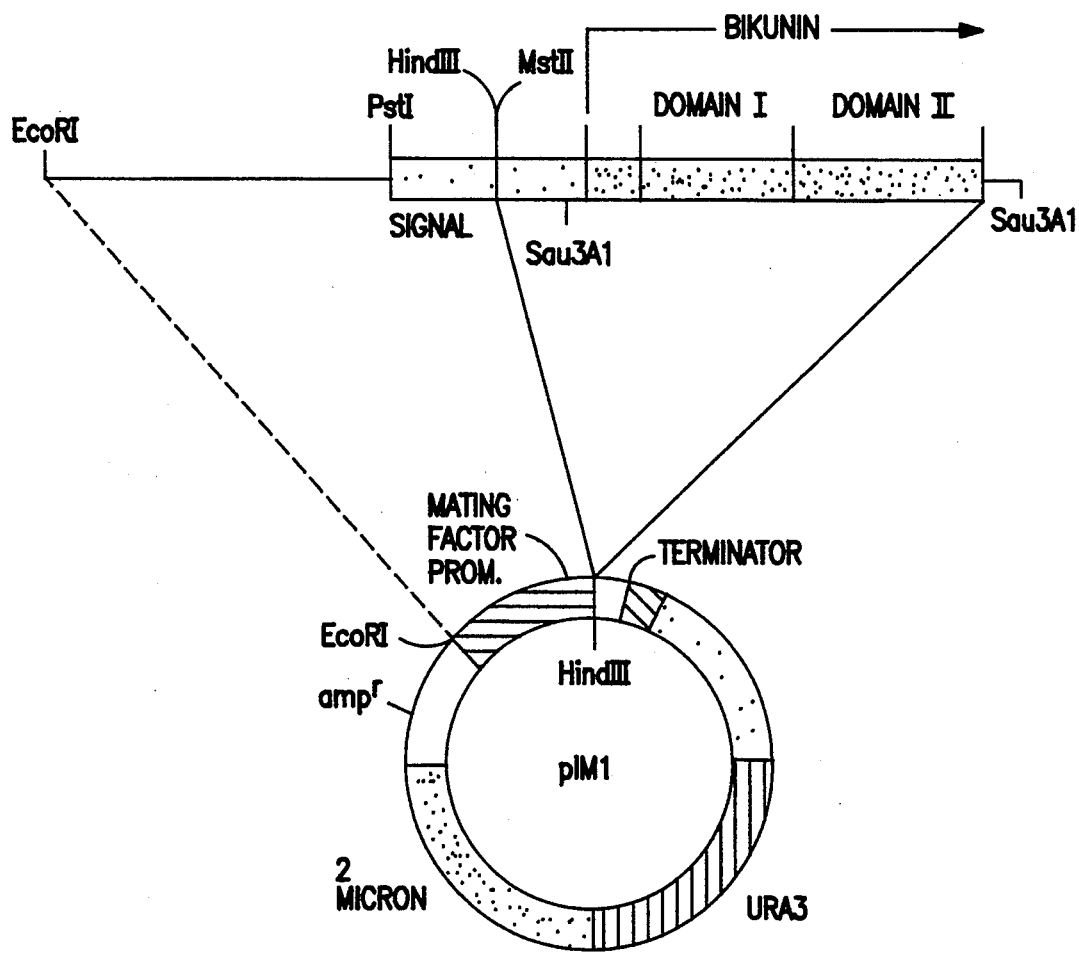

FIG. 13 schematically depicts the naturally occurring bikunin gene cloned into the pMT15 E.coli-yeast shuttle vector which contains the alpha-factor pre-pro-sequence.

Figure 14:
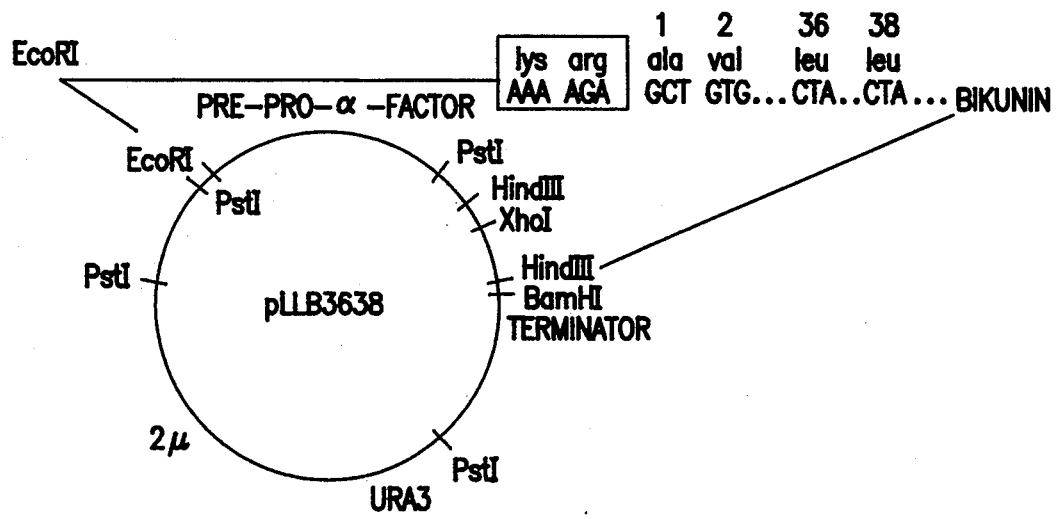

FIG. 14 schematically depicts expression vector pLLB3638. Pre-pro-alpha-factor-Leu-36-Leu-38-bikunin gene fusion cloned into the vector pS600. DNA sequence and corresponding amino acid sequence at the fusion site of pre-pro-alpha-factor-Leu-36-Leu-38-bikunin in pLLB3638 is shown. Lys-Arg is the KEX2 processing site of the pre-pro-alpha-factor sequence (Julius et al., Cell, 37, 1075, 1984). The amino acid numbering 1–38 corresponds to that in the bikunin mutein sequence.

Figure 15:
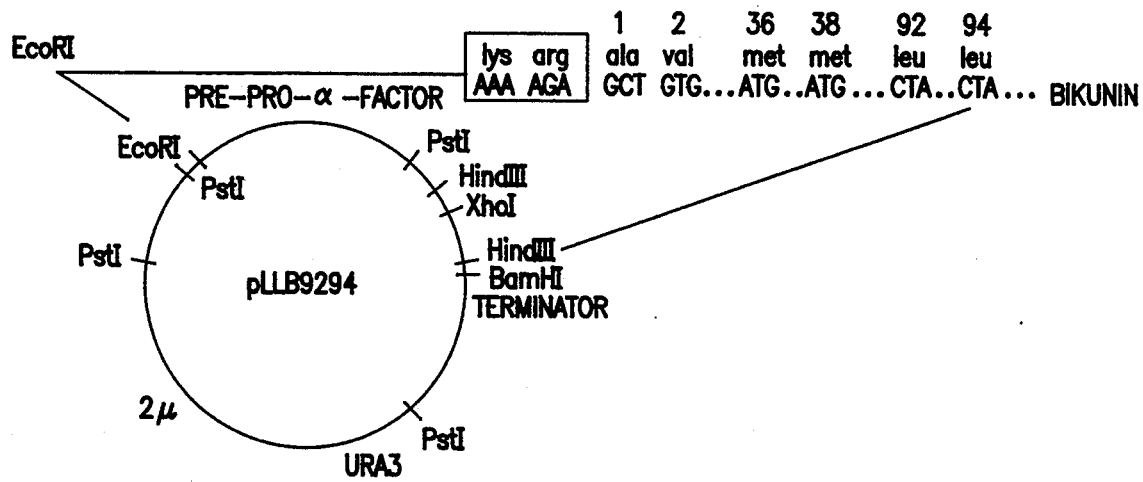

FIG. 15 schematically depicts expression vector pLLB9294. Pre-pro-alpha-factor-Leu-92-Leu-94-bikunin gene fusion cloned into the vector pS600. DNA sequence and corresponding amino acid sequence at the fusion site of pre-pro-alpha-factor-Leu-92-Leu-94-bikunin in pLLB3638 is shown. Lys-Arg is the KEX2 processing site of the pre-pro-alpha-factor sequence (Julius et al., Cell, 37, 1075, 1984). The amino acid numbering 1–94 corresponds to that in the bikunin mutein sequence.

Figure 16:
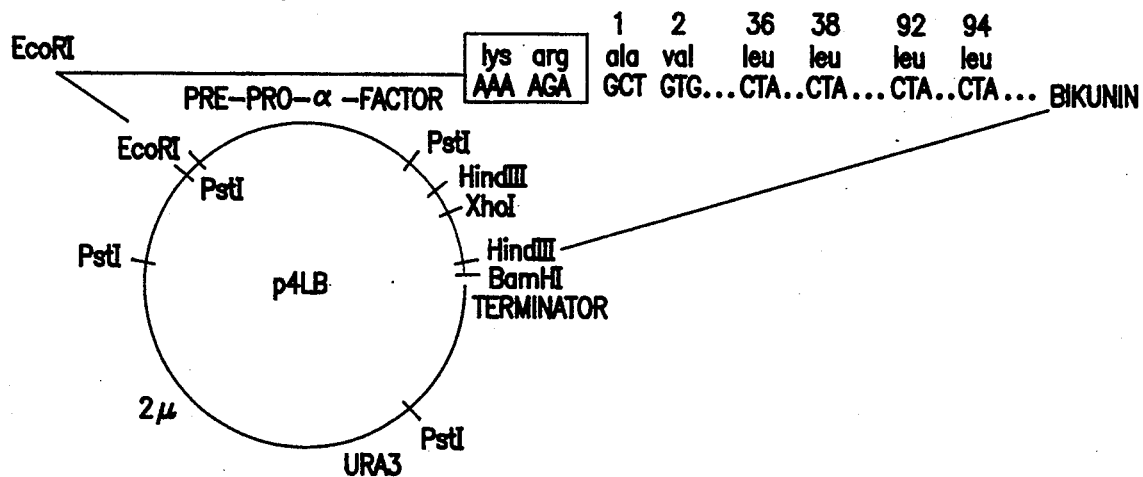

FIG. 16 schematically depicts expression vector p4LB. Pre-pro-alpha-factor-Leu-36-Leu-38-Leu-92-Leu-94-bikunin gene fusion cloned into the vector pS600. DNA sequence and corresponding amino acid sequence at the fusion site of pre-pro-alpha-factor-Leu-36-Leu-38-Leu-92-Leu-94-bikunin in p4LB is shown. Lys-Arg is the KEX2 processing site of the pre-pro-alpha-factor sequence (Julius et al., Cell. 37, 1075, 1984). The amino acid numbering 1–94 corresponds to that in the bikunin mutein sequence.

Figure 17:
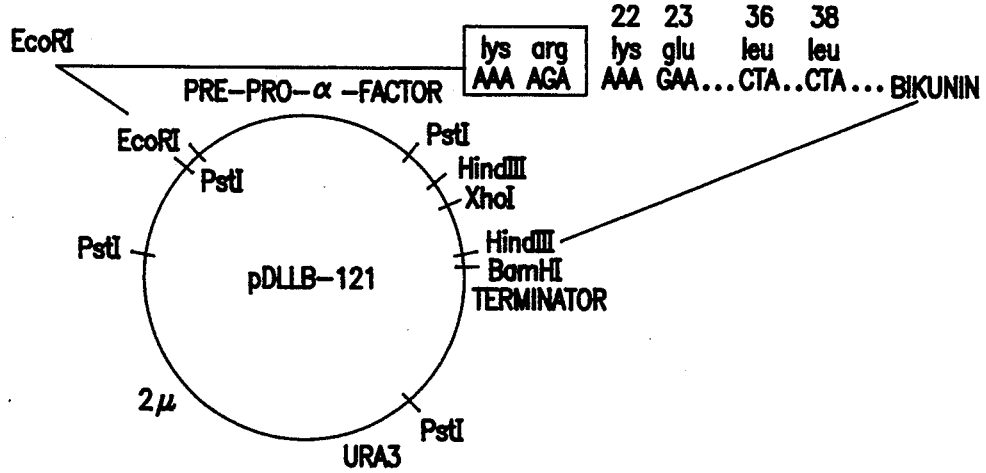

FIG. 17 schematically depicts expression vector pDLLB-121. Pre-pro-alpha-factor-de(1-21) -Leu-36-Leu-38-bikunin gene fusion cloned into the vector pS600. DNA sequence and corresponding amino acid sequence at the fusion site of pre-pro-alpha-factor-de(1-2 1 ) -Leu-36 -Leu-38-bikunin in pDLLB- 12 1 is shown. Lys-Arg is the KEX2 processing site of the pre-pro-alpha-factor sequence (Julius et al., Cell, .37, 1075, 1984). The amino acid numbering 1–38 corresponds to that in the bikunin mutein sequence.

It will be appreciated that the instant specification is set forth by way of illustration and not limitation, and that various modification and changes may be made without departing from the spirit and scope of the present invention.

What is claimed is:

1. A proteinase inhibitor having the amino acid sequence 21 to 147 of human bikunin and having one or more of the replacements selected from the group consisting of positions 36, 38, 92, 94, 98 and 116, wherein
   the Met position 36 is replaced by Arg, Phe, Tyr, Trp or Lys;
   the Met at position 38 is replaced by Arg or Lys;
   the Arg at position 92 is replaced by Leu, Ile, Val or Phe;
   the Phe at position 94 is replaced by Leu, Arg, Lys, Ile or Val;
   the Trp at position 98 is replaced by Lys, Ils, Val, Leu, Ala, Gly or Ser; and
   the Gln at position 116 is replaced by Arg or Lys.

2. A proteinase inhibitor according to claim 1, with or without glycosylation.

3. A pharmaceutical composition comprising an effective amount of the proteinase inhibitor according to claim 1 and a pharmaceutically acceptable diluent.

4. A method of inhibiting proteinase activity in a patient, comprising administering to the patient a proteinase inhibitory effective amount of a proteinase inhibitor according to claim 1.

5. A proteinase inhibitor having the amino acid sequence 1 to 147 of human bikunin and having one or more of the replacements selected from the group consisting of positions 36, 38, 92, 94, 98 and 116, wherein
   the Met at position 36 is replaced by Arg, Phe, Tyr, Trp or Lys;
   the Met at position 38 is replaced by Arg or Lys;
   the Arg at position 92 is replaced by Leu, Ile, Val or Phe;
   the Phe position 93 is replaced by Leu, Arg, Lys, Ile or Val;
   the Trp at position 98 is replaced by Lys, Ile, Val, Leu, Ala, Gly or Ser; and
   the Gln at position 116 is replaced by Arg or Lys.

6. A proteinase inhibitor according to claim 5, with our without glycosylation.

7. A pharmaceutical composition comprising an effective amount of the proteinase inhibitor according to claim 5 and a pharmaceutically acceptable diluent.

8. A method of inhibiting proteinase activity in a patient, comprising administering to the patient a proteinase inhibitory effective amount of a proteinase inhibitor according to claim 5.

9. A fragment having proteinase inhibitory activity, said fragment having the amine acid sequence selected from the group consisting of amino acids 22 to 77, 1 to 77 or 78 to 147 of human bikunin and having one or more replacements selected from the group consisting of positions 36, 38 and 94, wherein
   the Met at position 36 is replaced by Arg, Phe, Tyr, Trp or Lys,
   the Met at position 38 is replaced by Arg or Lys; and
   the Phe at position 94 is replaced by Leu, Arg, Lys, Ile or Val.

10. A proteinase inhibitor according to claim 9, with our without glycosylation.

11. A pharmaceutical composition comprising an effective amount of the proteinase inhibitor according to claim 9 and a pharmaceutically acceptable diluent.

12. A method of inhibiting proteinase activity in a patient, comprising administering to the patient a proteinase inhibitory effective amount of a proteinase inhibitor according to claim 9.

13. A fragment having proteinase inhibitory activity according to claim 9 wherein the fragment having amino acids 78–147 further comprises one or more of the replacements selected from the group consisting of positions 92, 98, and 116, wherein the Arg at position 92 is replaced by Leu, Ile, Val, or Phe;

the Trp at position 98 is replaced by Lys, Ile, Val, Leu, Ala, Gly, or Ser; and the Gln at position 116 is replaced by Arg or Lys.

14. A proteinase inhibitor according to claim 13, with or without glycosylation.

15. A pharmaceutical composition comprising an effective amount of the proteinase inhibitor according to claim 13 and a pharmaceutically acceptable diluent.

16. A method of inhibiting proteinase activity in a patient, comprising administering to the patient a proteinase inhibitory effective amount of a proteinase inhibitor according to claim 13.

* * * * *

UNITED STATES PATENT AND TRADEMARK OFFICE
CERTIFICATE OF CORRECTION

PATENT NO. : 5,407,915
DATED : April 18, 1995
INVENTOR(S) : Fritz, et al.

It is certified that error appears in the above-indentified patent and that said Letters Patent is hereby corrected as shown below:

| | |
|---|---|
| Col. 18, line 5 | After " Met " insert -- at -- |
| Col. 18, line 33 | After " Phe " insert -- at --, delete " 93 " and substitute -- 94 -- |
| Col. 18, line 39 | Delete " our " and substitute -- or -- |
| Col. 18, line 48 | Delete " amine " and substitute -- amino -- |
| Col. 18, line 59 | Delete " our " and substitute -- or -- |

Signed and Sealed this

Eighteenth Day of July, 1995

Attest:

BRUCE LEHMAN

*Attesting Officer*    *Commissioner of Patents and Trademarks*